(12) United States Patent
von Blumenthal et al.

(10) Patent No.: US 7,985,198 B2
(45) Date of Patent: Jul. 26, 2011

(54) DEVICE AND PROCESS FOR METERING SOLUTIONS

(75) Inventors: Tilman von Blumenthal, Lübeck (DE); Stefan Zimmermann, Lübeck (DE); Götz Kullik, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1286 days.

(21) Appl. No.: 11/424,661

(22) Filed: Jun. 16, 2006

(65) Prior Publication Data

US 2007/0073273 A1 Mar. 29, 2007

(30) Foreign Application Priority Data

Sep. 23, 2005 (DE) .......................... 10 2005 045 393

(51) Int. Cl.
*A61M 5/14* (2006.01)
*A61M 31/00* (2006.01)
*A61K 9/22* (2006.01)

(52) U.S. Cl. .......................... 604/80; 604/65; 604/890.1
(58) Field of Classification Search .................. 604/65, 604/80, 246, 258, 890.1; 141/104
See application file for complete search history.

(56) References Cited

U.S. PATENT DOCUMENTS 4,925,444 A 5/1990 Orkin et al.

*Primary Examiner* — Nicholas D Lucchesi
*Assistant Examiner* — Victoria P Campbell
(74) *Attorney, Agent, or Firm* — McGlew and Tuttle, P.C.

(57) ABSTRACT

A process and device for metering different solutions is provided with which a high rate of repetition of drugs to be metered is possible. To accomplish the object, provisions are made for taking fluid volumes in the range of 50 nL to 50 μL from a fluid source (2, 3, 4, 5) in rapid succession in time according to the time multiplex method and for introducing them into a collecting channel (10) without mixing.

19 Claims, 15 Drawing Sheets

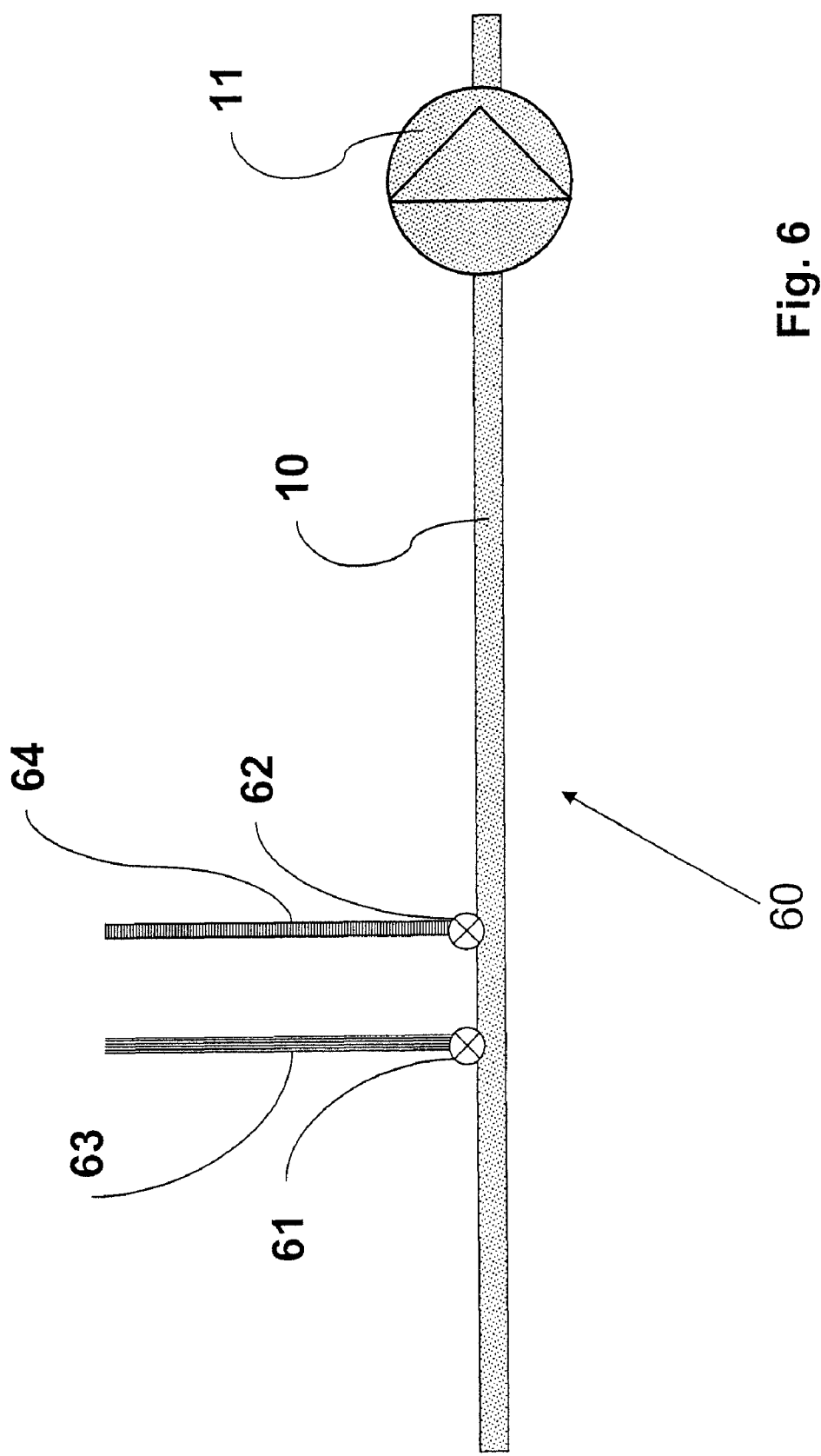

DEVICE AND PROCESS FOR METERING SOLUTIONS

CROSS REFERENCE TO RELATED APPLICATIONS

This application claims the benefit of priority under 35 U.S.C. §119 of German Patent Application 10 2005 045 393.7 filed Sep. 23, 2005, the entire contents of which are incorporated herein by reference.

FIELD OF THE INVENTION

The present invention pertains to a device and a process for metering solutions in a time multiplex manner.

BACKGROUND OF THE INVENTION

A device of this type is known from U.S. Pat. No. 4,925,444. The prior-art infusion system offers the possibility of metering different solutions from fluid sources according to the multiplex method into a common collecting channel. A typical metering cycle at a rate of metering of 50 mL per hour lasts about 40 sec. If the cycle time is reduced, a higher flow rate is necessary, which is permissible as a short-term bolus in exceptional cases only.

Catecholamines with blood plasma half-lives of less than 2 minutes must be metered either continuously or quasi-continuously at intervals shorter than 15 sec. The smallest metered quantity is about 1 µL.

Other drugs are titrated by the physician according to their action; for example, in the case of remifentanil, the rate of metering is changed as a function of the depth of anesthesia. A change in the rate of metering must have reached the patient within a few seconds in the case of these drugs. Such drugs cannot be metered with the prior-art infusion system because of the long rinsing times. Incompatible drugs can also be transported through the same patient line in exceptional cases only with the prior-art infusion system. The desired separation between individual drugs can be achieved with difficulty only. A parabolic flow profile will rather develop in the patient line, which leads to nearly complete mixing on the transport path.

SUMMARY OF THE INVENTION

The basic object of the present invention is to provide a process for metering different solutions, which makes possible a high rate of repetition.

According to the invention, a process is provided for metering liquids from a plurality of fluid sources in a time-multiplex manner according to a fluid release plan into a common patient line. The process includes the selection of a fluid source and removal of the fluid volumes in the range of 50 nL to 50 µL. A fluid stream is formulated from a sequence of the fluid volumes of at least two said different fluid sources. The individual metered volumes for each solution are added up to a total volume. A comparison is made of the total volumes administered for each solution with the fluid release plan in order to minimize deviations.

The advantage of the present invention is essentially that the portion size of the drugs being metered is reduced to the extent that the metering of one portion contains markedly less active ingredient than the target quantity of the active ingredient in the blood circulation even in the case of quickly and intensely acting drugs. For example, the minimum target quantity in the blood at a low dosage is approx. 5 µg in the case of the catecholamine norepinephrine. At a usual concentration of 100 µg per mL, the target quantity in the blood will consequently correspond to a drug portion size of approx. 50 µL. If, by contrast, undiluted drug is used, this quantity may be even considerably lower.

Helpful is the metering of drug portions of different drugs with predefined volume into a common line, in which the size of the smallest drug portions used is in the range of 50 nL to 50 µL. Especially advantageous is likewise the metering of drug portions of different drugs with predefined size into a common line, in which the enclosed system volume, through which at least two solutions flow from different storage containers, from the point of confluence to the entry into the patient's bloodstream, is smaller than 0.7 mL. A system volume in the range smaller than 0.3 mL is especially advantageous here.

In case of metering drug portions of different drugs with a predefined size into a common line, a mean flow rate of 50 mL per hour will usually become established. A mean velocity of at least 7 cm per second is advantageous. A mean velocity of at least 13 cm per second is advantageous.

Immiscible drugs are advantageously separated by a separating medium. A lipid liquid is advantageously used as the separating liquid. Soybean oil is also a suitable separating liquid. It is also possible to use as the separating medium gases, for example, air, oxygen, nitrogen, carbon dioxide or water vapor. It should be borne in mind in case of using gases that the metered gas volume does not exceed the value of 1 mL within 15 minutes.

The drugs to be metered can be fed into a common collecting channel in different ways. It is possible in this connection to associate an active pump with each drug line. Suitable pumps are, for example, peristaltic micropumps, with which a stroke volume between 50 nL and 50 µL can be obtained. An alternative possibility of metering is to take a drug portion with a calibrating volume from the fluid source and then feed same into the collecting channel.

If actively delivering pumps are arranged in each drug line, high costs may arise, because the element determining the precision must assume both the metering function and the transport function. A total flow pump is therefore advantageously arranged in the connecting channel, and the drug lines are provided with on-off valves, which are briefly opened to release a certain portion of drug into the collecting channel. Fluidic flow resistances in the form of metering capillaries may be associated with the on-off valves.

The metering of the drugs is precise if the fluidic resistance is exactly known in each drug line and the vacuum that becomes established is determined in the collecting channel and is also included in the evaluation.

Metering capillaries made of glass or silicon, as they are known from laboratory practice, can be used especially advantageously for metering. To minimize the effect of changes in viscosity during temperature changes, all metering capillaries are thermally controlled. As an alternative, the temperature may also be measured and compensated by calculation.

It is especially advantageous to use two pumps arranged in series for metering the drug and for transporting same over the patient line and into the patient. The first pump now operates as a precision pump and delivers the drug from a rigid collecting chamber into a soft intermediate chamber, while the second pump takes the drug from the intermediate chamber and delivers same into the patient line. The soft intermediate chamber is used to equalize the pressure between the pump used to meter the drug and the total flow pump, and thus it ensures that the drug metering area is subject to small pressure differences ranging from a few multiples of 10 mbar to a few multiples of 100 mbar only. By contrast, the delivery pressure in the patient line for transporting the drugs to the patient is a few bar.

To reduce the dead space volume, the patient line is designed such that its cross-sectional area is in a range between 0.02 mm² and 0.2 mm² at least in some sections, which corresponds to a diameter between 0.05 mm and 0.5 mm.

Metering valves for feeding drugs into the common collecting channel are advantageously arranged directly at the collecting channel. As a result, the drugs can be released directly into the collecting channel, without mixing reactions taking place at the site of feeding in. Dead volumes of <10 μL can thus be obtained.

Metering elements for a plurality of drugs and the corresponding collecting channel and, if necessary, also flow- and pressure-measuring systems are advantageously arranged on a common carrier plate in the form of a microfluid metering system.

The carrier plate has connections for drug lines as well as two connections for passing through the collecting channel. Due to the use of a common carrier plate, dead space volumes within the metering system can be further reduced.

To prevent the velocity of the drug from becoming too low, a small line cross section of the patient line is especially advantageous in case of the metering of drugs with a low flow rate. On the other hand, a small line cross section means a great pressure drop at high flow rates. It is therefore advantageous to select a material for the patient line that increases the cross-sectional area by at least 10% at flow rates between 100 mL per hour and 200 mL per hour compared to the cross-sectional area without flow. This can be achieved by the use of a flexible tube material that stretches in a pressure-dependent manner.

Pressure measurement is necessary in the collecting channel for the accurate monitoring of metering. The sterility of the drugs being metered must not be compromised by the pressure measurement. A hydrophobic bacteria filter, which is arranged upstream of the pressure pick-up, is advantageously used for the pressure measurement. The liquid phase in the collecting channel is separated hereby from the gas phase in the area in which the pressure is measured.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6 is a schematic view of a drug-metering system in which the pinch valves are arranged in the connection area to the collecting channel;

DESCRIPTION OF THE PREFERRED EMBODIMENTS

Figure 1:
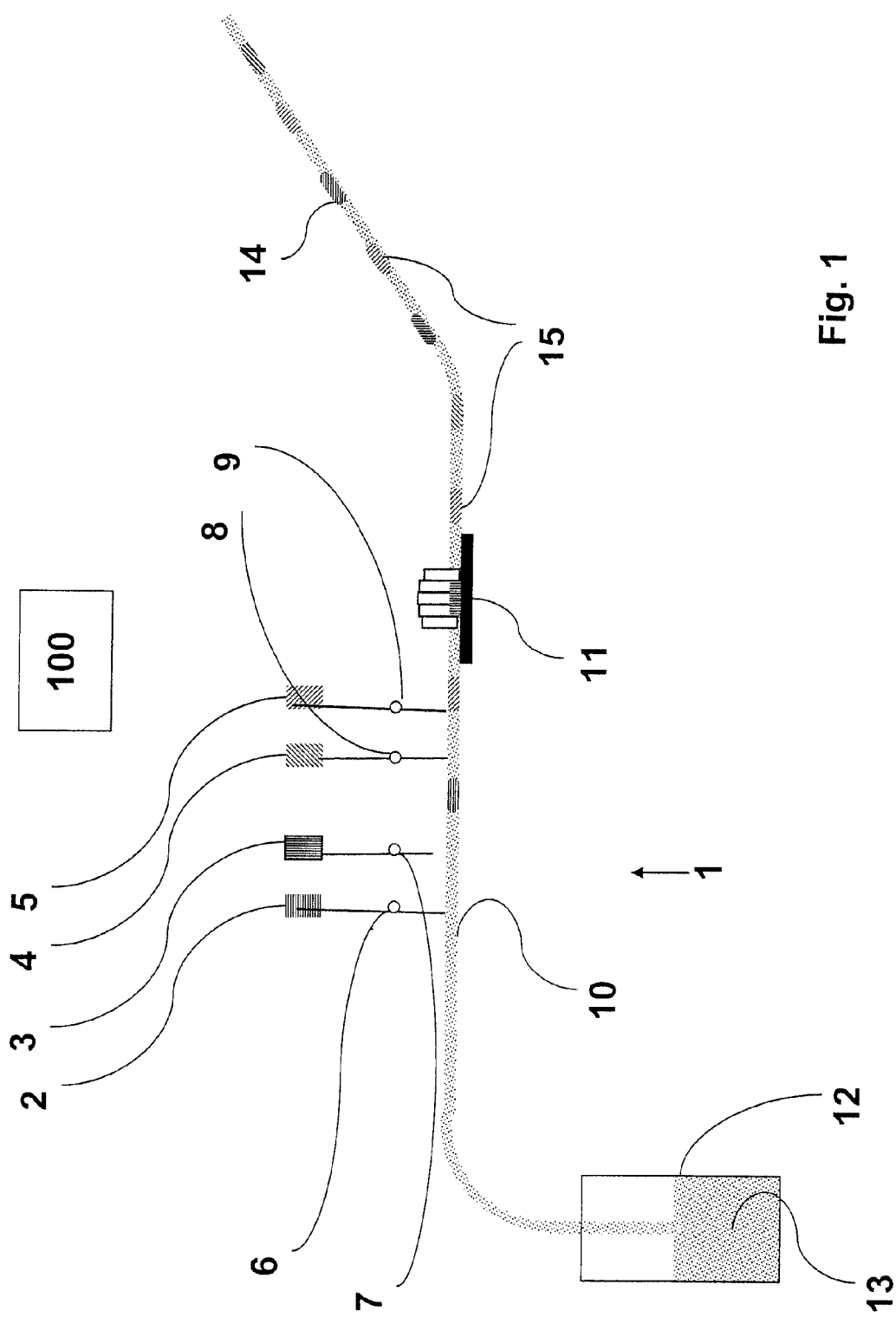
FIG. 1 is a schematic view of an infusion system according to the present invention.

Referring to the drawings in particular, FIG. 1 schematically illustrates the design of an infusion system 1 for metering drugs from four fluid sources 2, 3, 4, 5. The fluid sources 2, 3, 4, 5 are connected via metering elements 6, 7, 8, 9 with a collecting channel 10. A pump 11 connected to the collecting channel 10 delivers carrier liquid 13 from a reservoir 12 into a patient line 14. The fluid sources 2, 3, 4, 5 contain different drugs, which are introduced into the collecting channel in portions according to a release plan. The drug boli 15, which are illustrated as an example in the patient line 14, are separated from one another by the carrier liquid 13. A control unit 100 is connected to the metering elements 6, 7, 8, 9 and the pump 11 and performs the metering of the drugs according to the multiplex method according to the fluid release plan. The control unit provides means for selecting the fluid source based on the fluid release plan. The total volume of each drug being metered is continuously determined and compared to the preset value in the fluid release plan. If deviations are now detected, the actuating signals for the metering elements 6, 7, 8, 9 are correspondingly adjusted.

Figure 2:
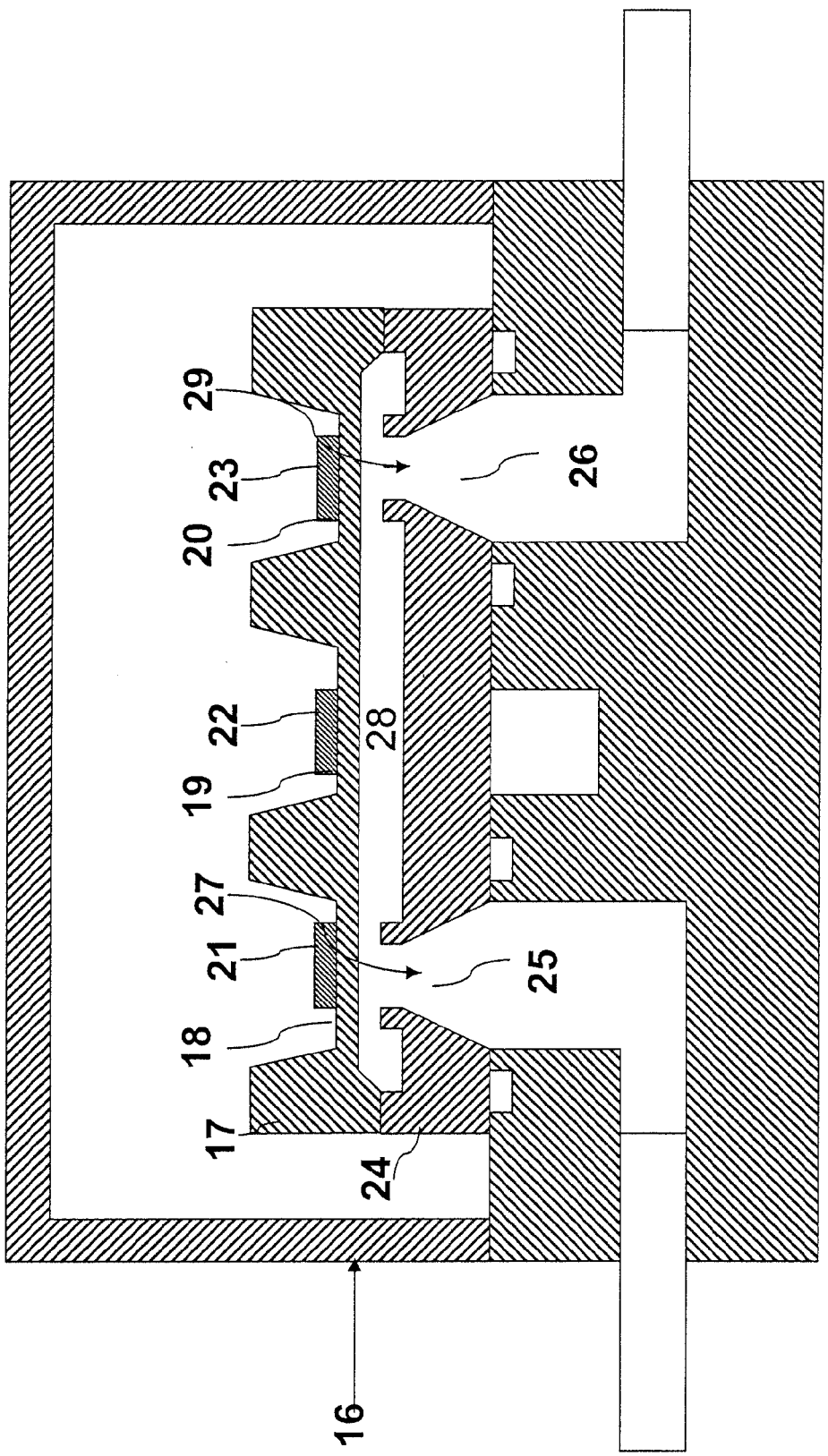
FIG. 2 is a longitudinal sectional view of a peristaltic micropump.

FIG. 2 shows the longitudinal section of a peristaltic micropump 16 as a metering element as it appears as an example from DE 102 38 600 A1. The micropump 16 comprises a membrane element 17 with three membrane sections 18, 19, 20. Each of the membrane sections 18, 19, 20 is provided with a piezo element 21, 22, 23 and forms separate piezo membrane transducers together with the membrane sections 18, 19, 20. A pump body 24 contains a fluid inlet 25 and a fluid outlet 26. An inlet valve 27, a pump chamber 28 and an outlet valve 29 are formed by the membrane sections 18, 19, 20 in connection with the pump body 24.

With the outlet valve 29 closed and the inlet valve 27 opened, the membrane section 19 of the pump chamber 28 is moved upward, and the drug to be metered is drawn up via the fluid inlet 25. The inlet valve 27 is then closed, the outlet valve 29 is opened and the drug volume is released via the fluid outlet 26, and the membrane section 19 is now moved downward. Volume strokes in the range of 0.1 µL, to 010 µL, can be performed with the prior-art micropump 16. The micropump 16 forms one embodiment of a means for removing fluid volumes.

Figure 3:
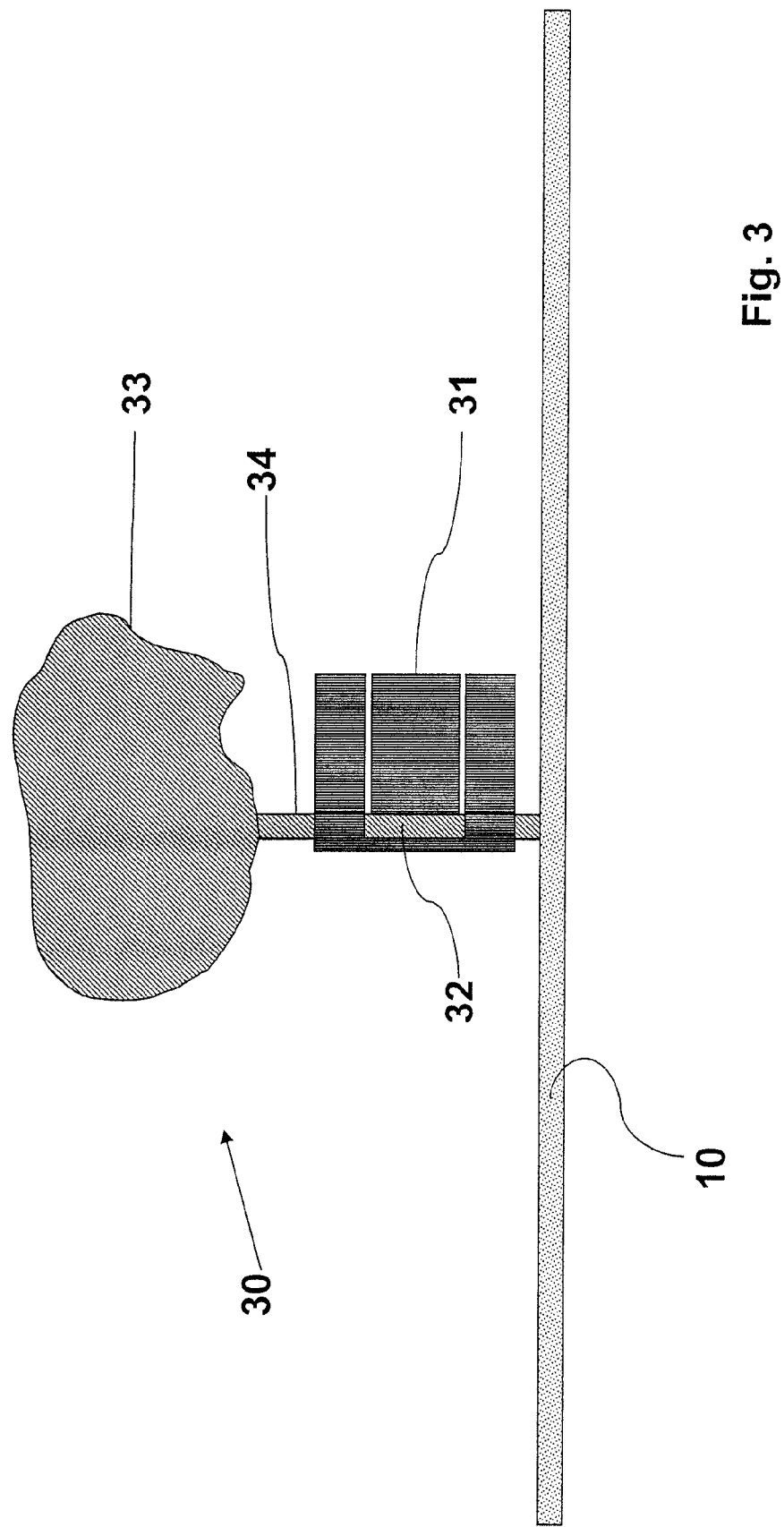
FIG. 3 is a schematic view of a drug metering system with a deformable tube section.

FIG. 3 illustrates an alternative metering element 30 in the form of an elastomer channel 32 deformable by a pump 31. The alternative metering element 30 forms a means for removing fluid volumes. The drug to be metered is accommodated in a fluid container 33 with low flexural strength. A defined, measured channel section 34 is filled with the drug and is subsequently emptied by the pump 31. The elastomer channel 32 has an internal cross section in the range of 0.1 mm$^2$ to 2 mm$^2$ and a wall thickness greater than 1 mm. The metered fluid volume is fed into the collecting channel 10 that forms a means for forming a fluid stream.

Figure 4:
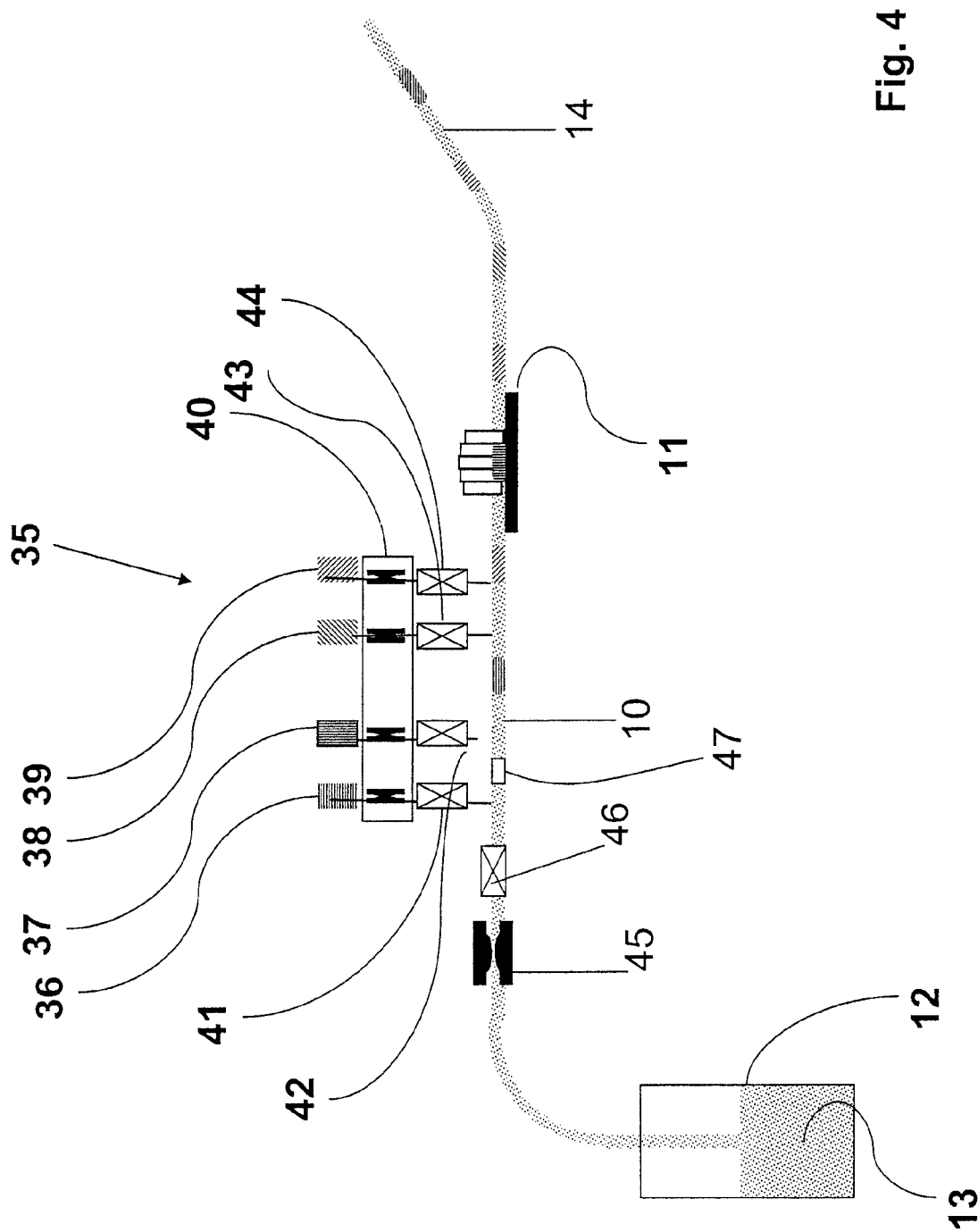
FIG. 4 is a schematic view of a drug metering system with metering capillaries.

FIG. 4 shows a drug metering system 35, in which drug containers 36, 37, 38, 39 are connected to the collecting channel 10 via temperature-stabilized metering capillaries 40 and corresponding on-off valves 41, 42, 43, 44 that form a means for removing fluid volumes. The collecting channel 10 (means for forming a fluid stream) is connected to the reservoir 12 for the carrier liquid 13 via a throttle 45. Another on-off valve 46 and a pressure-measuring device 47 are located on the discharge side of the throttle 45. The pump 11 delivers the fluid stream into the patient line 14.

The metering capillaries 40, which are schematically illustrated as a block only in FIG. 4, consist of glass or silicon with a cross-sectional area smaller than 0.05 mm$^2$. The fluidic resistance is more than 50 mbar per 1,000 mm per hour and typically 50 mbar per 20 mL per hour.

To meter drug volumes, a defined vacuum is generated with the pump 11, and this vacuum is measured with the pressure-measuring device 47. By opening one of the valves 41, 42, 43, 44 for a predetermined time interval, the drug to be metered is drawn in from one of the drug containers 36, 37, 38, 39. By briefly opening the valve 46 in the collecting channel 10, carrier liquid can subsequently be delivered before a new drug volume is metered. By temporarily closing the on-off valve 46 in the collecting channel 10, the rate of delivery of the carrier solution can be reduced if needed.

Figure 5A:
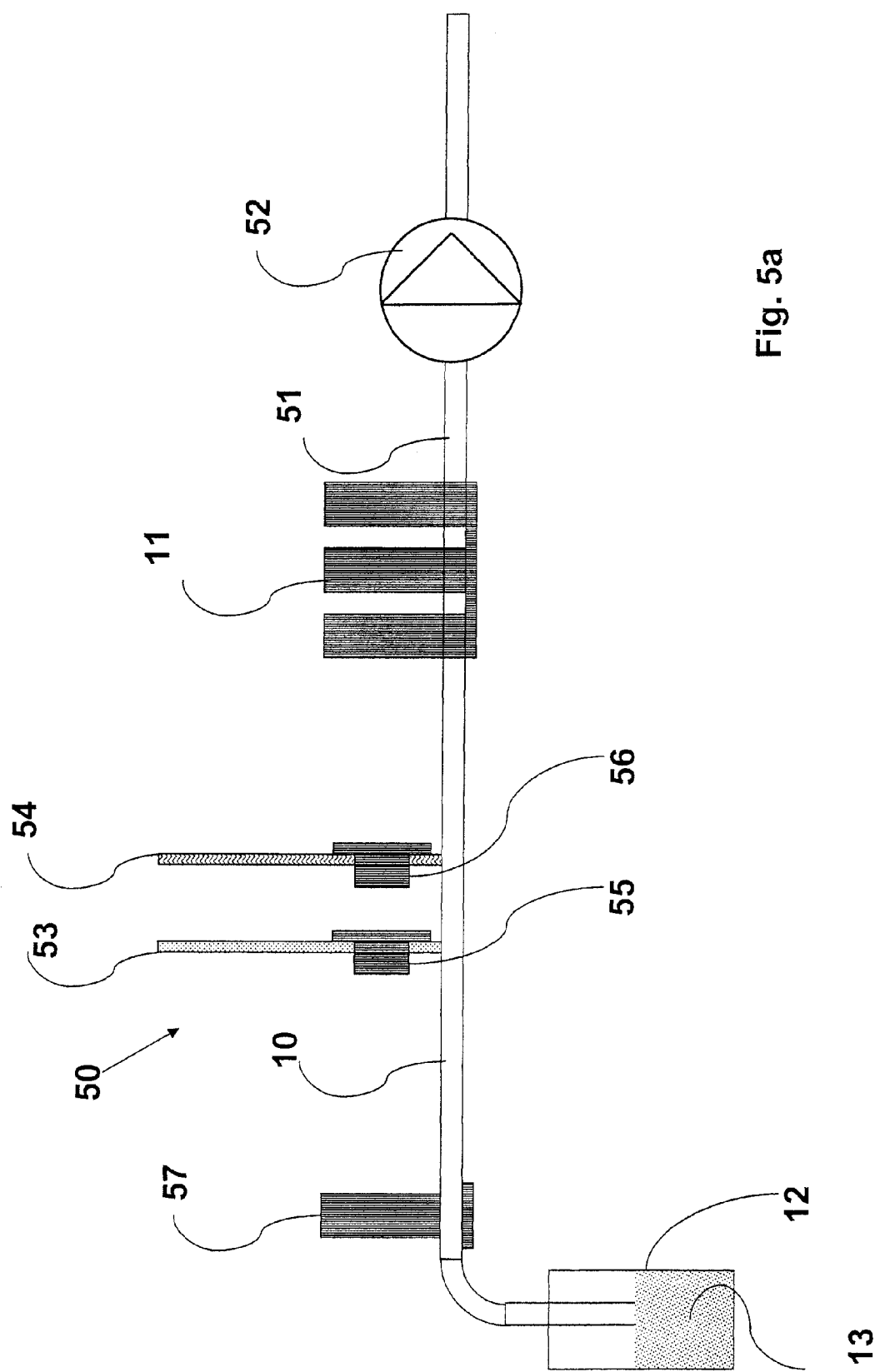
FIG. 5a is a schematic view showing a drug-metering system with pinch valves in the drug lines and two delivery pumps connected in series.
Figure 5B:
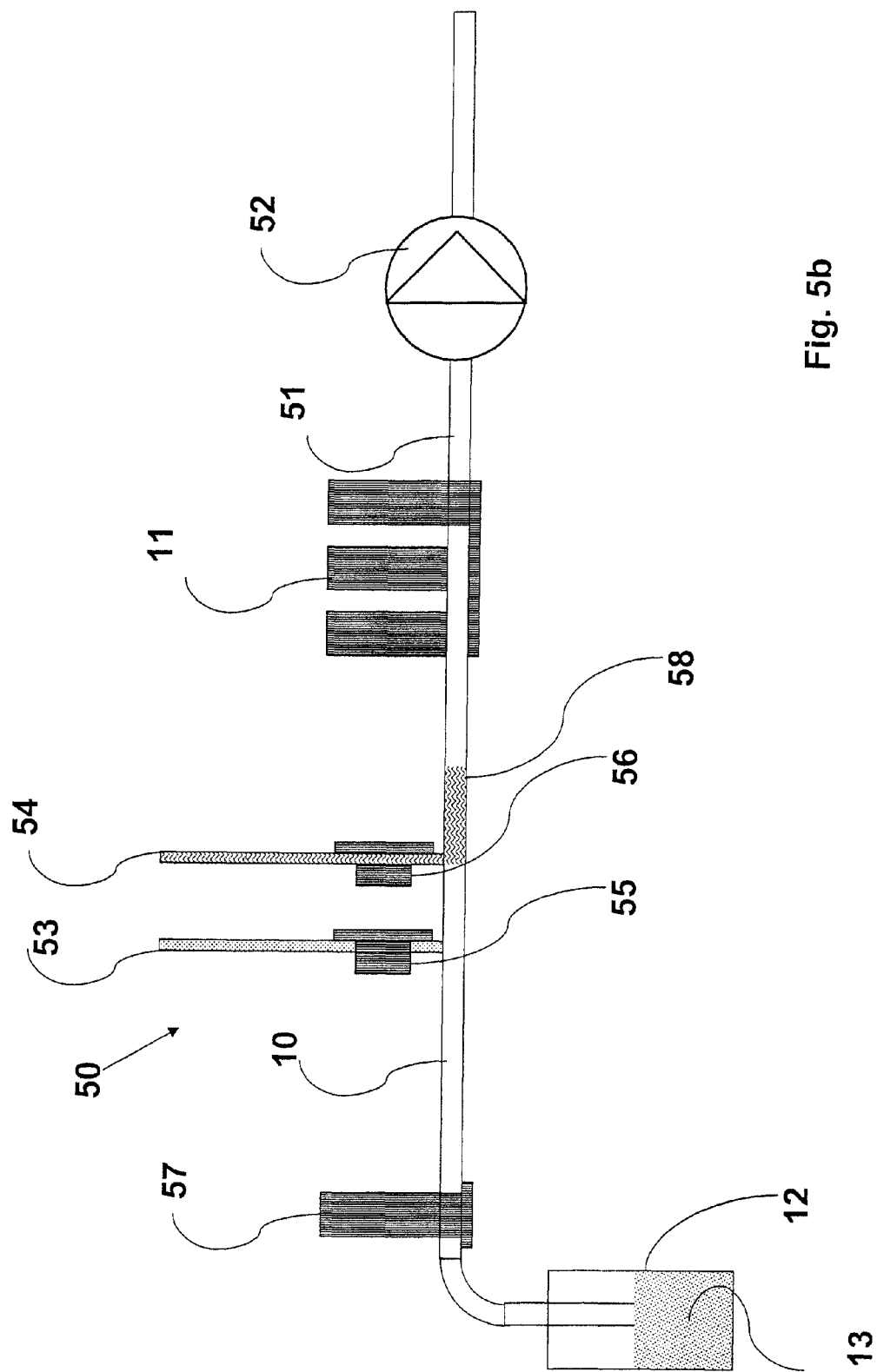
FIG. 5b is a schematic view showing a drug-metering system with pinch valves in the drug lines and two delivery pumps connected in series.
Figure 5C:
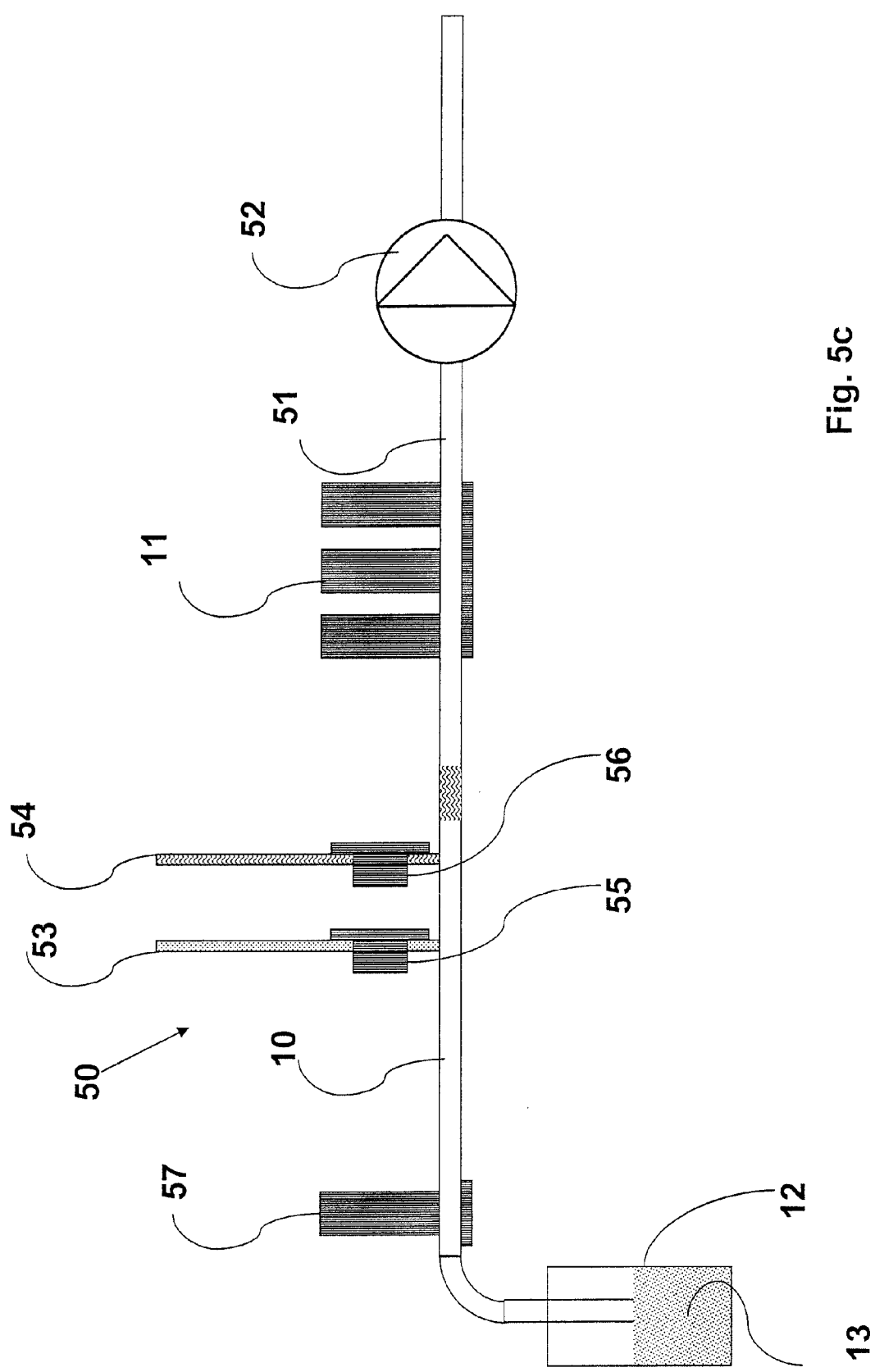
FIG. 5c is a schematic view showing a drug-metering system with pinch valves in the drug lines and two delivery pumps connected in series.

FIGS. 5a-5c schematically show a drug metering system 50, in which a total flow pump 52 is arranged downstream of the pump 11 via a flexible intermediate chamber 51. Two drug lines 53, 54 are connected to the collecting channel 10 consisting of solid material via pinch valves 55, 56 (means for removing fluid volumes). Another pinch valve 57 is located in the collecting channel 10 on the side on which the flow in the drug lines 53, 54 arrives.

The pump 11 delivers from the rigid collecting channel 10 into the soft mixing chamber 51 to the inlet of the total flow pump 52.

The soft intermediate chamber 51 is used to equalize the pressure in case of transient differences between the flow rates of the pump 11 and the total flow pump 52 and it thus ensures that the pump 11 is exposed to small pressure differences ranging from a few multiples of 10 mbar to a few multiples of 100 mbar only. The delivery pressure proper for transporting the drugs to the patient is a few bar and is generated by the less precise total flow pump 52.

The course of metering over time is shown in FIGS. 5a through 5c.

In FIG. 5a, the pinch valve 57 is opened and the carrier flow in the collecting channel 10 is stagnant. The pinch valve 57 is closed and the pinch valve 56 of the drug line 54 is opened in FIG. 5b, so that the pump 11 transports a predefined drug volume 58 into the collecting channel. The rigid collecting channel 10 with a compliance of <100 nL per mbar ensures that exactly as much drug is taken from the drug line 54 as is drawn in by the pump 11. The pinch valve 57 is opened and the pinch valve 56 is again closed in FIG. 5c. The drug volume 58 is transported with the carrier liquid 13 by the pump 11 into the collecting channel 10. After the metering of the drug, pump 11 opens and carrier liquid is delivered exclusively via the less precise total flow pump 52. Pressure equalization is achieved as a result in the intermediate chamber 51.

According to an advantageous variant of a drug metering system 60 shown in FIG. 6, pinch valves 61, 62 (fluid volume removal means) are placed in the connection area between the drug lines 63, 64 and the collecting channel 10. Metering that is controlled over time is thus achieved, and a mixing reaction in the dead space between the solution in the collecting channel 10 and the pinch valves 55, 56, FIG. 5, is avoided. The dead space can be reduced to a value of less than 50 nL with the drug metering system 60 corresponding to FIG. 6. The pinch valves 61, 62 consist of elastomeric materials, which can be closed by compression.

Figure 7:
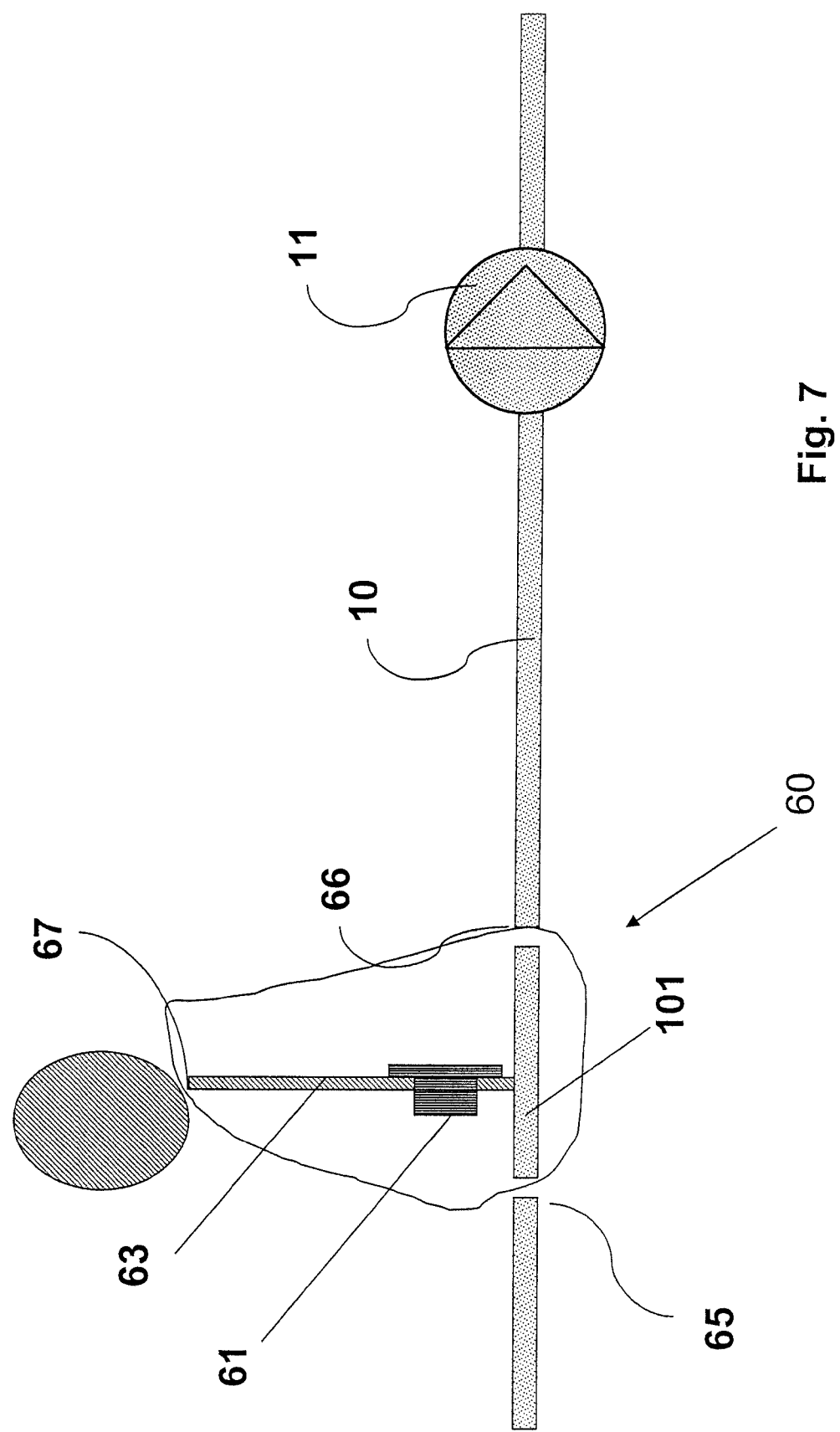
FIG. 7 is the drug metering system according to FIG. 6 with additional connectors.

Part of the drug line 63, the pinch valve 61 and a collecting channel section 101 are made in one piece and integrated into the overall system via contact points 65, 66, 67 in a variant of the drug metering system 60 according to FIG. 6, which is illustrated in FIG. 7.

Figure 8:
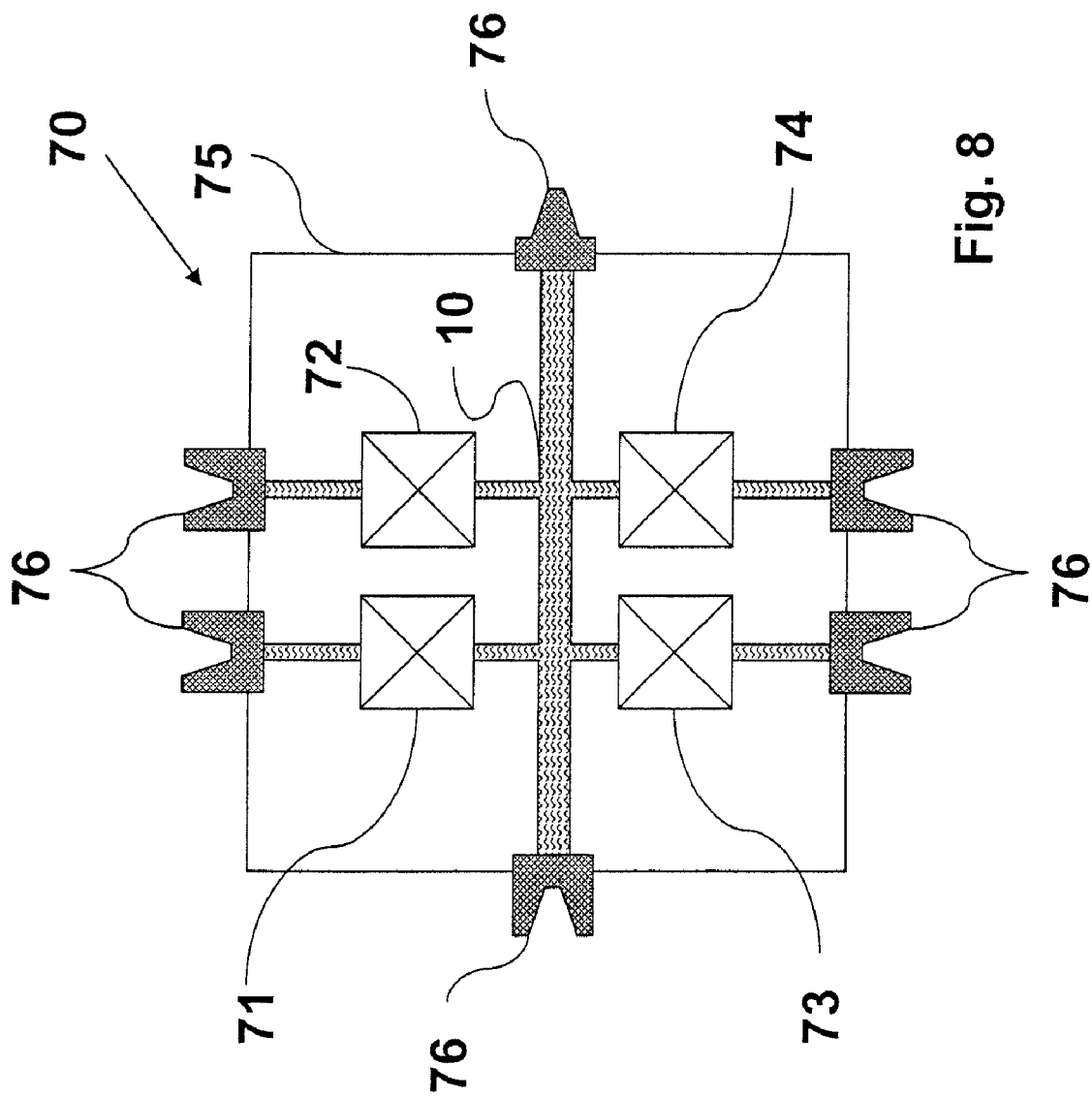
FIG. 8 is a schematic view showing a micrometering system on a carrier plate.

The pinch valves 71, 72, 73, 74 (fluid volume removal means) and the collecting channel 10 are arranged on a common carrier plate 75 in the form of a micrometering system in a drug metering system 70 shown in FIG. 8. The connection to the peripheral components is performed via so-called Luer Lock connections 76.

Figure 9:
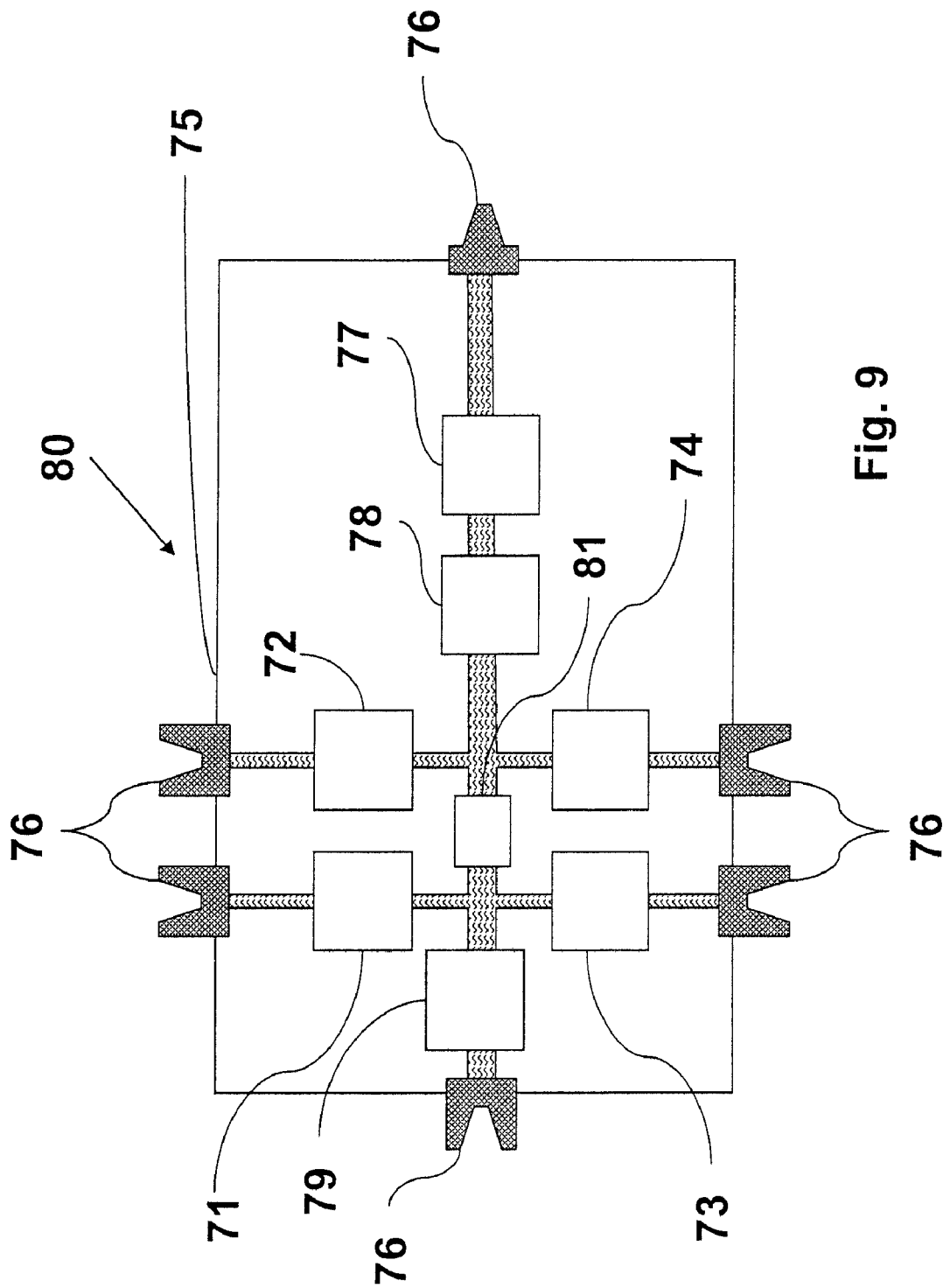
FIG. 9 is a schematic view showing the micrometering system according to FIG. 8 with additional actuators.

FIG. 9 illustrates an alternative drug metering system 80 to the drug metering system 70 according to FIG. 8, in which a pump 77, closing valves 78, 79 and a pressure-measuring device 81 are additionally arranged on the carrier plate 75. Identical components are designated by the same reference numbers as in FIG. 8.

Figure 10A:
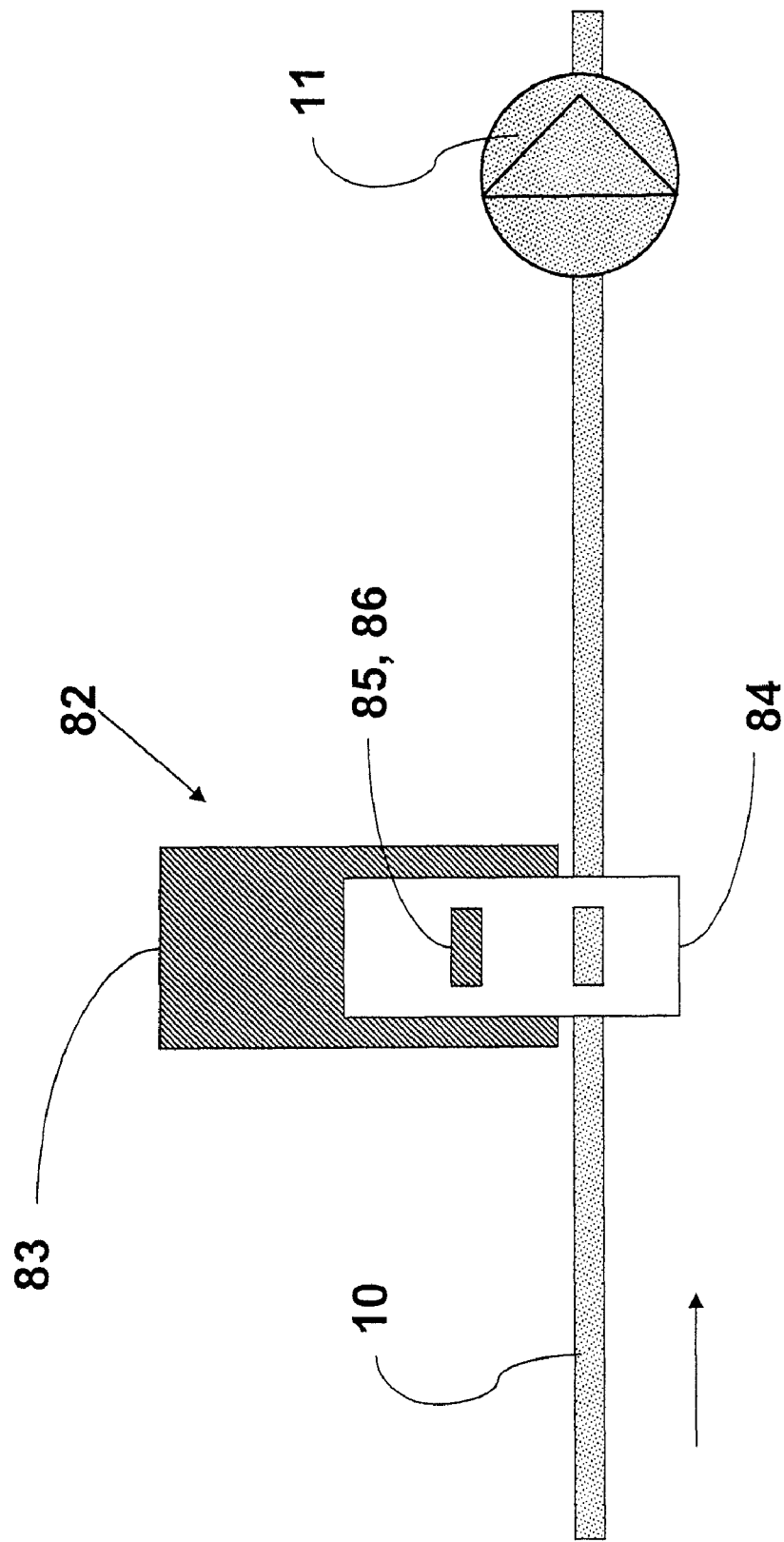
FIG. 10a is a schematic view showing a drug-metering system with drug metering via a calibrating volume.
Figure 10B:
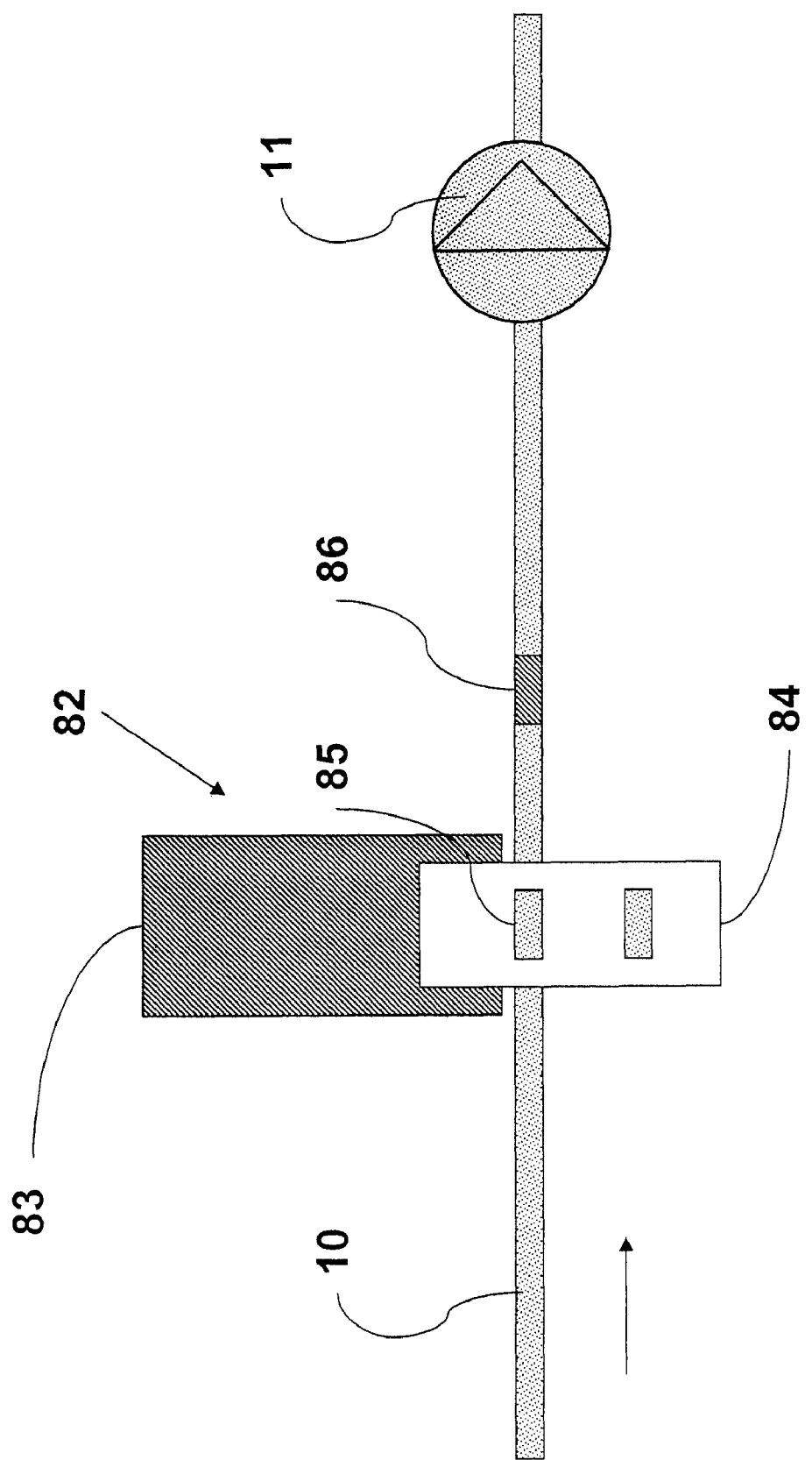
FIG. 10b is a schematic view showing a drug-metering system with drug metering via the calibrating volume.

FIG. 10a shows a metering device 82, in which a drug volume 86 is taken from a drug container 83 by means of a slide 84 that forms the means for removing fluid volumes). The slide 84 has a recess 85 for this in the form of a calibrating volume, which recess is filled with the drug. FIG. 10a illustrates the filling of the recess 85, and the release of the drug into the collecting channel 10 is illustrated in FIG. 10b.

Figure 11:
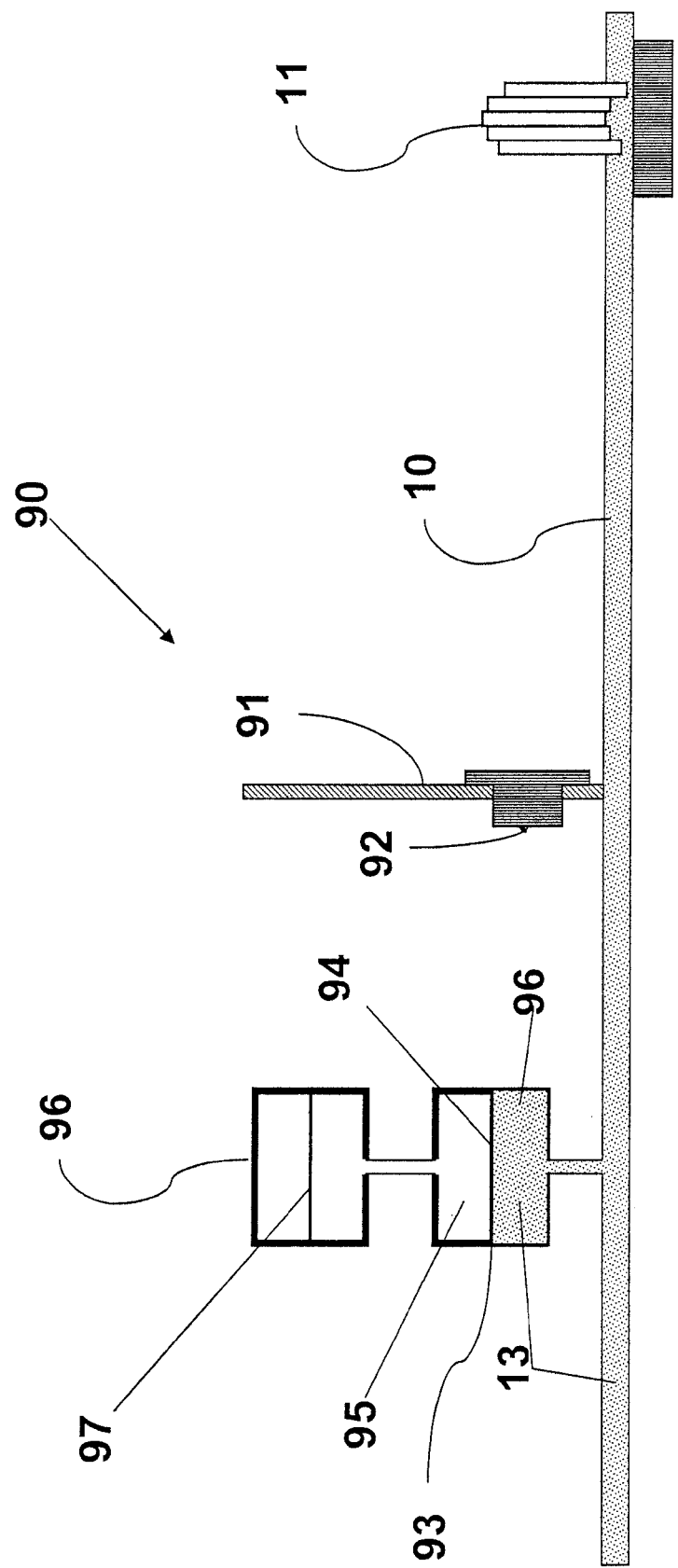
FIG. 11 is a schematic view showing a drug-metering system with sterile pressure measurement.

FIG. 11 shows as an example a sterile pressure measurement in a drug metering system 90, which contains the collecting channel 10, a drug line 91 with a pinch valve 92 and the pump 11. A volume 93 is divided by a hydrophobic membrane 94, which is permeable to gas, into two chambers 95, 96. The upper chamber 95 is connected to a pressure pick-up 96 with the measuring membrane 97.

The lower chamber 96 is in flow connection with the collecting channel 10 and is filled with the carrier liquid 13.

Figure 12:
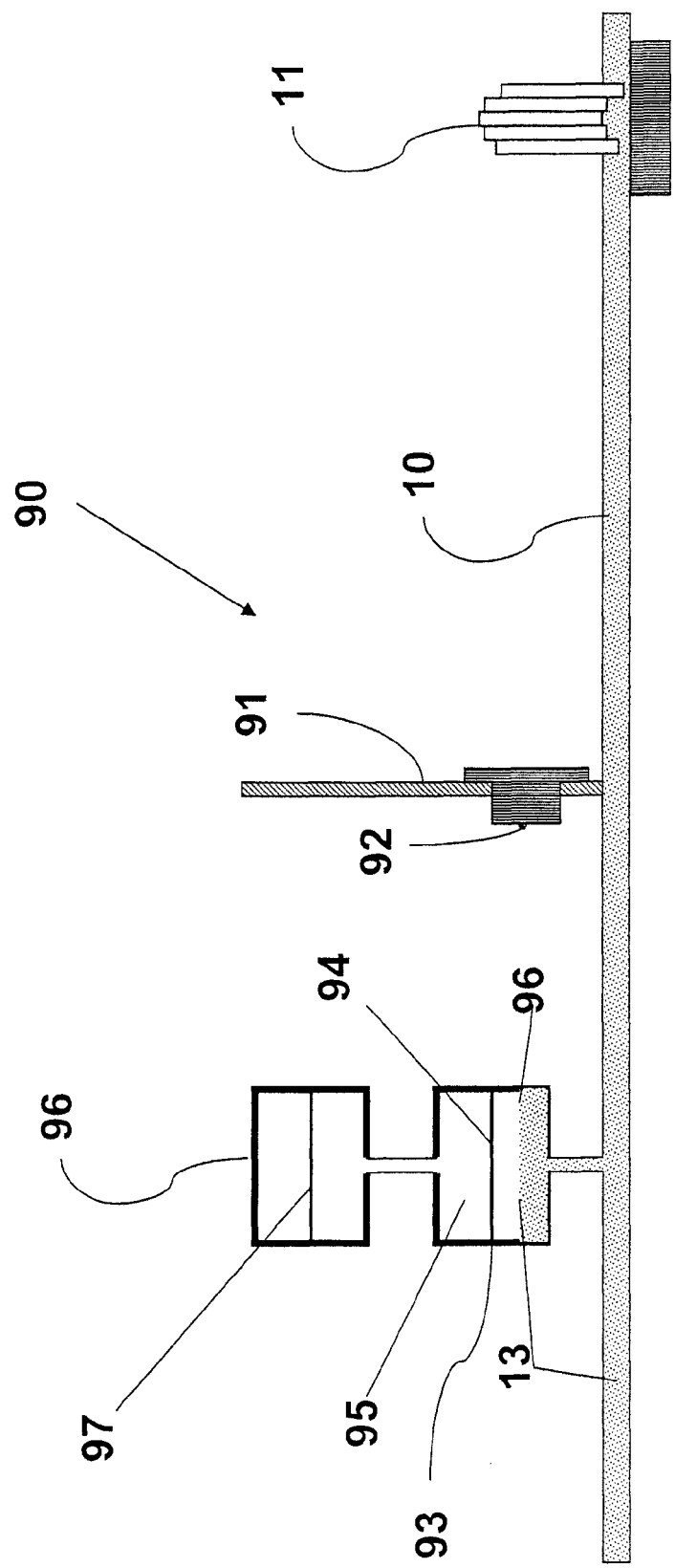
FIG. 12 is a schematic view showing a drug-metering system according to FIG. 11 with vacuum generation in the collecting channel.

When the pump 11 draws in, the volume of gas in the upper chamber 96 increases and the membrane 94 is exposed, so that the hydrostatic pressure of the carrier liquid 13 acts directly on the measuring membrane 97. This state is illustrated in FIG. 12. Sterile separation of the pressure measurement from the delivery of fluid is brought about by the membrane 94.

While specific embodiments of the invention have been shown and described in detail to illustrate the application of the principles of the invention, it will be understood that the invention may be embodied otherwise without departing from such principles.

What is claimed is:

1. A process for metering liquids from a plurality of fluid sources, in a time-multiplex manner according to a fluid release plan, into a common patient line, the process comprising the steps of:
   providing a common patient line having a cross-sectional area in a range between 0.002 mm² and 0.2 mm², which corresponds to a diameter between 0.05 mm and 0.5 mm in case of a circular cross section;
   providing a carrier liquid reservoir with a carrier liquid, the common patient line having carrier liquid therein and being in fluid connection with the carrier liquid reservoir;
   connecting each of the plurality of fluid sources to the common patient line by a respective metering passage;
   selecting at least two fluid sources according to a fluid release plan;
   removing fluid volumes in the range of 50 nL to 50 μL from each of the selected fluid sources;
   forming a fluid stream from a sequence of the fluid volumes of at least two different said fluid sources in the common patient line, wherein fluid volumes of immiscible solutions are separated by a separation medium to provide discrete boluses of the fluid volumes flowing out of the common patient line to a patient with the fluid volumes remaining separated by the separation medium and in a particular order as they flow through the common patient line to the patient;
   adding up of the individual metered fluid volumes for each source to determine a total volume; and
   comparing the total volumes administered for each solution with the fluid release plan in order to minimize deviations.

2. A process in accordance with claim 1, wherein the separating medium is selected from the group comprising lipid liquids, soybean oil and gases such as air, oxygen, nitrogen, carbon dioxide or water vapor.

3. A process in accordance with claim 1, wherein the removing of fluid volumes and the forming a fluid stream from a sequence of the fluid volumes includes metering the fluid volumes by a delivery means associated with the fluid sources.

4. A process in accordance with claim 3, wherein the delivery means is a micropump.

5. A process in accordance with claim 3, wherein the fluid volume is taken from the fluid source with a calibrating volume.

6. A process in accordance with claim 3, wherein the fluid volume is taken from the fluid source with the metering passage comprising a pinchable elastomer channel providing on-off valve.

7. A process in accordance with claim 3, wherein the delivery means or valves associated with the delivery means are arranged at the point at which a fluid line opens into a collecting channel.

8. A process in accordance with claim 1, wherein the fluid volumes are taken with a pump arranged in the patient line via valves, each valve being arranged downstream of the respective fluid source.

9. A process in accordance with claim 8, wherein the valves contain fluidic flow resistances in the form of metering capillaries contributing to a known fluidic resistance.

10. A device for metering according to a fluid release, the device comprising:
    a plurality of fluid sources;
    a common patient line with a cross-sectional area that is, at least in some sections, in a range between 0.002 mm² and 0.2 mm², which corresponds to a diameter d between 0.05 mm and 0.5 mm in case of a circular cross section;
    a carrier liquid reservoir with a carrier liquid therein, the common patient line having carrier liquid therein and being in fluid connection with the carrier liquid reservoir;
    a plurality of metering passages, each of the plurality of fluid sources being connected to the common patient line by a respective metering passage;
    a means for selecting fluid sources according to the fluid release plan;
    a means for removing fluid volumes in the range of 50 nL to 50 μL from the selected fluid sources and forming a fluid stream from a sequence of the fluid volumes of at least two said different fluid sources, wherein fluid volumes of immiscible solutions are separated by a separation medium to provide discrete boluses of the fluid volumes flowing out of the common patient line to a patient with the fluid volumes remaining separated by the separation medium and in a particular order as they flow through the common patient line to the patient;
    a control for adding up of the individual metered volumes for each source to determine a total volume and for comparing the total volumes administered for each solution with the fluid release plan in order to minimize deviations.

11. A device in accordance with claim 10, wherein the means for removing individual fluid volumes from said fluid sources includes a corresponding collecting channel arranged on a common carrier plate in the form of a microfluid metering system.

12. A device in accordance with claim 10, wherein said means for removing individual fluid volumes includes a delivery means associated with the fluid sources.

13. A device in accordance with claim 12, wherein the delivery means is a micropump.

14. A device in accordance with claim 12, wherein the fluid volume is taken from the fluid source with a calibrating volume.

15. A device in accordance with claim 12, wherein the metering passage comprises a pinchable elastomer channel.

16. A device in accordance with claim 12, wherein the delivery means or valves associated with the delivery means are arranged at a collecting channel connected to or forming a part of the patient line.

17. A device in accordance with claim 10, wherein said means for removing individual fluid volumes includes a pump arranged in the patient line via valves, each valve being arranged downstream of the respective fluid source.

18. A device in accordance with claim 17, wherein the valves contain fluidic flow resistances in the form of metering capillaries contributing to a known fluidic resistance.

19. A device for metering liquids from a plurality of said fluid sources, in a time-multiplex manner according to a fluid release plan, into a common patient line, the device comprising:
    means for selecting fluid sources;
    means for removing fluid volumes in the range of 50 bL to 50 μL from the selected fluid sources and forming a fluid stream from a sequence of the fluid volumes of at least two said different fluid sources;
    a control unit for adding up of the individual metered volumes for each source to determine a total volume and for comparing the total volumes administered for each solution with the fluid release plan in order to minimize deviations wherein:

said means for removing individual fluid volumes includes a pump arranged in the patient line via valves, each valve being arranged downstream of the respective fluid source; and the valves contain fluidic flow resistances in the form of metering capillaries.

* * * * *